(12) United States Patent
Jiang et al.

(10) Patent No.: US 6,734,974 B2
(45) Date of Patent: May 11, 2004

(54) TERAHERTZ IMAGING WITH DYNAMIC APERTURE

(75) Inventors: Zhiping Jiang, Ottawa (CA); Qin Chen, Emmaus, PA (US); Xie George Xu, Clifton Park, NY (US); Xi-Cheng Zhang, Latham, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 74 days.

(21) Appl. No.: 10/056,866

(22) Filed: Jan. 25, 2002

(65) Prior Publication Data

US 2002/0153874 A1 Oct. 24, 2002

Related U.S. Application Data

(60) Provisional application No. 60/263,722, filed on Jan. 25, 2001.

(51) Int. Cl.[7] .......................... G01N 21/00; G01N 21/17

(52) U.S. Cl. ....................... 356/432; 356/433; 356/434; 250/330; 250/358.1; 250/341.1

(58) Field of Search ............................ 356/432, 433, 356/434; 250/330, 358.1, 341.1, 208.1, 201.3, 216, 237 G

(56) References Cited

U.S. PATENT DOCUMENTS

| | | | | |
|---|---|---|---|---|
| 5,623,145 A | * | 4/1997 | Nuss | 250/330 |
| 5,710,430 A | * | 1/1998 | Nuss | 250/358.1 |
| 5,894,125 A | | 4/1999 | Brener et al. | 250/330 |
| 6,111,416 A | * | 8/2000 | Zhang et al. | 324/753 |
| 6,356,349 B1 | * | 3/2002 | Koehl et al. | 356/432 |

OTHER PUBLICATIONS

"A Microwave Magnetic Microscope," by R. F. Soohoo; *Journal of Applied Physics*, Supplement to vol. 33, No. 3; Mar. 1962 (pp. 1276–1277).

"Super–resolution Aperture Scanning Microscope," by E. A. Nash and G. Nicholls; *Nature*, vol. 237; Jun. 30, 1972 (pp. 06–08).

"Contras of Microwave Near–field Microscopy," by B. Knoll, F. Keilmann, A. Kramer, and R. Guckenberger; *Appl. Phys. Lett. 70 (20);* May 19, 1997 (pp. 2667–2669).

"Near–Field Optics: Microscopy, Spectroscopy, and Surface Modification Beyond the Diffraction Limit," By Eric Betzig and Jay K. Trautman; *Science*, vol. 257; Jul. 10, 1992 (pp. 189–195).

"THz near–field imaging," by S. Hunsche, M. Koch, I. Brener, and M. C. Nuss; *Optics Communications* 150; 1998 (pp. 22–26).

"Superluminal terahertz pulses," by Klaas Wynne and Dino A. Jaroszynski; *Optics Letters*, vol. 24, No. 1; Jan. 1, 1999 (pp. 25–27).

(List continued on next page.)

*Primary Examiner*—Frank G. Font
*Assistant Examiner*—Roy M Punnoose
(74) *Attorney, Agent, or Firm*—RatnerPrestia

(57) ABSTRACT

A method of improving spatial resolution of a pump-probe terahertz (THz) imaging system for producing an image of an object. The method provides a chopped optical gating beam focused on a semiconductive layer that is either part of the object or a discrete layer placed over the object. The gating beam is focused on a gating pulse focal spot having a diameter effective to cause measurable modulation in transmission of a THz beam through the semiconductive layer when the gating pulse is on as compared to when the gating pulse is off, creating alternating modulated THz beams for detection and processing. Systems for performing the method in transmission and reflection modes are also described.

46 Claims, 15 Drawing Sheets

OTHER PUBLICATIONS

"Two–photon absorption induced saturation of THz radiation in ZnTe," by F. G. Sun, W. Ji, X.–C. Zhang; *Thursday Afternoon/CLEO 2000;* May 11, 2000 (pp. 479–480).

"Terahertz near–field microscopy based on a collection mode detector," by O. Mitrofanov, I. Brener, R. Harel, J. D. Wynn, L. N. Pfeiffer, K. W. West and J. Federici; *Applied Physics Letters*, vol. 77, No. 22; Nov. 27, 2000 (pp. 3496–3498).

"Infrared conductivity mapping for nanoelectronics," by B. Knoll and F. Keilmann; *Applied Physics Letters*, vol. 77, No. 24; Dec. 11, 2000 (pp. 3980–3982).

"IR microscopy with a transient photo–induced near–field probe (tipless near–field microscopy)" by Daniel V. Palanker, Guido M. H. Knippels, Todd I. Smith, H. Alan Schwettman; *Optics Communications 148;* Mar. 15, 1998 (pp. 215–220).

"Near–field microscope probe for far infrared time domain measurements," by Q. Mitrofanov, I. Brener, M. C. Wanke, R. R. Ruel, J. D. Wynn, A J. Bruce, and J. Federici; *Applied Physics Letters*, vol. 77, No. 4; Jul. 24, 2000 (pp. 591–593).

* cited by examiner

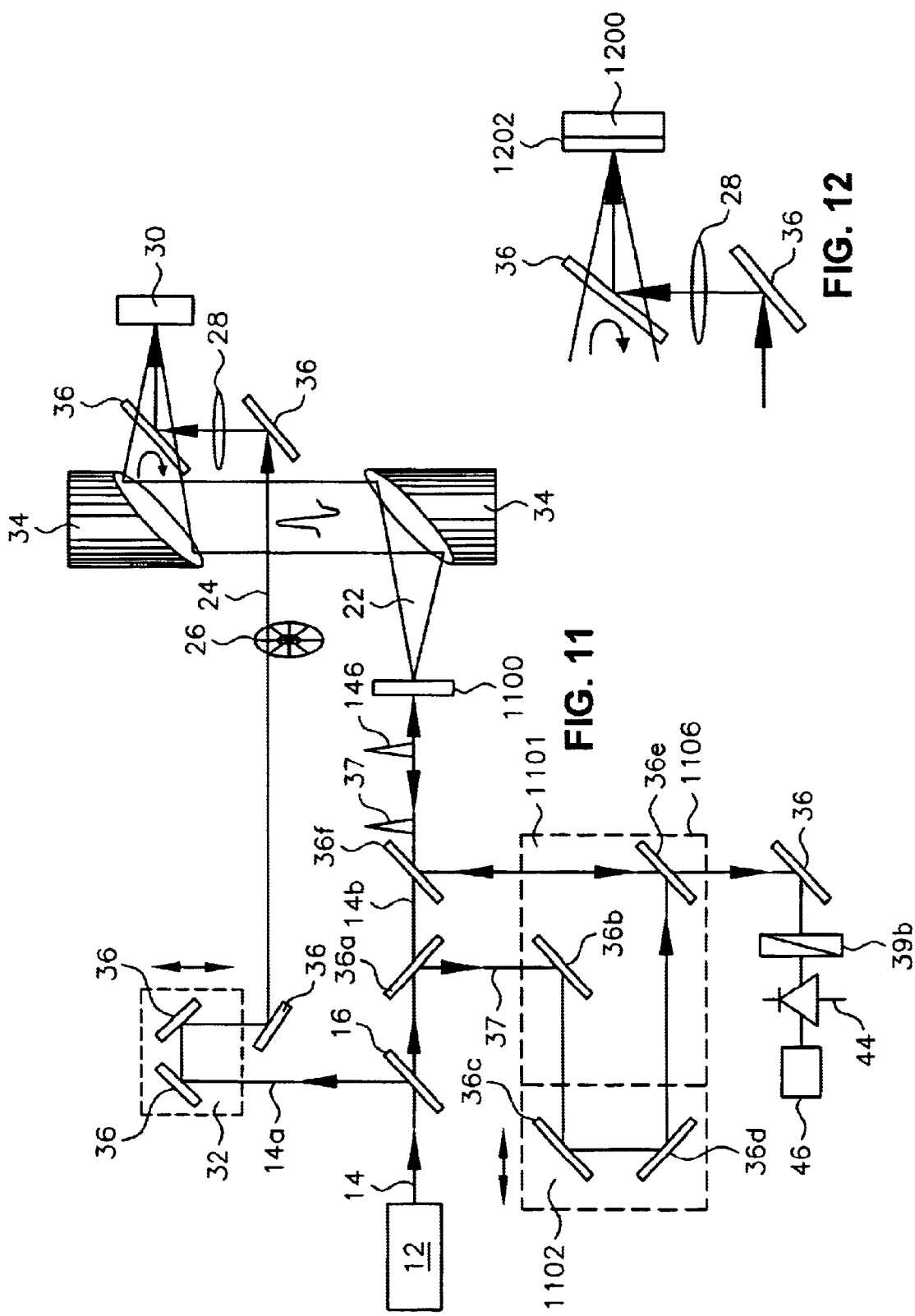

TERAHERTZ IMAGING WITH DYNAMIC APERTURE

CROSS-REFERENCE TO RELATED APPLICATIONS

This application claims the benefit of priority to U.S. Provisional Application Ser. No. 60/263,722, titled "Near-Field Terahertz Imaging With A Dynamic Aperture," filed on Jan. 25, 2001, and incorporated in this application by reference.

GOVERNMENT RIGHTS

The U.S. Government has a paid-up license in the present invention and the right in limited circumstances to require the patent owner to license others on reasonable terms as provided for by the terms of a contract awarded by the U.S. Army Research Office under funding numbers DAAD199910333 and DAAD1999C0045.

TECHNICAL FIELD

The present invention relates generally to imaging in the terahertz (THz) frequency range and, more specifically, to a method for improving the resolution of electro-optic terahertz imaging.

BACKGROUND OF THE INVENTION

The technique of imaging is generally understood as the measurement and replication of the intensity distribution of an active source emitting an electromagnetic wave or the backscattering profile of a passive object or scene. The functionality of imaging can be greatly extended by incorporating spectroscopy techniques in the imaging system. For example, organic functional groups in an imaged specimen can be identified and imaged by their select patterns of absorption wavelength. Microwave imaging and optical imaging are well-known and have been long used in the art.

Compared with the long history of microwave and optical imaging, however, terahertz (THz) wave imaging based on optoelectronic THz time-domain spectroscopy is in its infancy, having only recently emerged within the last six years. THz radiation occupies a large portion of the electromagnetic spectrum between the infrared (IR) and microwave bands, namely the frequency interval from 0.1 to 10 THz. Professor Zhang, a co-inventor of the present invention, holds a number of patents in this field, including U.S. Pat. Nos. 5,952,818, 6,057,928, and 6,111,416, all of which are incorporated in this application by reference for their basic teachings.

THz time-domain spectroscopy (THz-TDS) is based on electromagnetic transients that are generated and detected opto-electrically by femtosecond laser pulses. These THz transients are typically single-cycle bursts of electromagnetic radiation of less than 1-ps duration. These THz transients have a spectral density that typically spans the range from below 0.1 THz to more than 3 THz, and a brightness that typically exceeds greatly that of conventional thermal sources, due to high spatial coherence.

The temporally gated detection technique allows direct measurement of the THz electric field in the time domain with a time resolution of a fraction of a picosecond (ps). The detection is thus "coherent," meaning that both the amplitude and the phase of the THz spectrum can be extracted from the Fourier transform of the detected THz time-domain waveform. This characteristic is very useful for applications that require the measurement of the real and imaginary parts of the dielectric function. The sensitivity of the gated detection technique is orders of magnitude higher than traditional incoherent detection. In addition to this benefit, time-gated coherent detection is immune to incoherent far-IR radiation, making it possible to perform spectroscopy of high-temperature materials even in the presence of strong blackbody radiation background.

There are two main mechanisms typically employed for the generation of THz radiation in a typical THz-TDS system: photoconduction and optical rectification. In the first, photoconductors switched by an ultrafast laser pulse function as a radiating antenna. Based on their structure, the antennas can be classified as elementary Hertzian dipole antennas, resonant dipole antennas, tapered antennas, transmission line antennas, or large-aperture antennas. For THz generation via optical rectification, electro-optic crystals are used as the THz source. With the incidence of an ultrafast pulse on the electro-optic crystals, the different frequency components within the bandwidth of the fundamental optical beam form a polarization that oscillates at the beat frequency between these frequency components. This time-varying dielectric polarization produces a transient dipole that radiates broadband electromagnetic waves. In comparison with the THz radiation from photoconductive antennas (PDAs), THz optical rectification radiation has less power, but shorter pulse duration and larger bandwidth. The average power level of THz optical rectification radiation can reach several microwatts, depending on the pump power of the ultrafast laser sources.

Free-space electro-optic sampling (FS-EOS) is a coherent detection scheme for THz radiation based on detection of the polarization change of the optical probe beam induced by the THz electric field via the electro-optic Pockels effect in an electro-optic crystal. The field-induced birefringence of the sensor crystal due to the applied electric field (THz wave) modulates the polarization ellipticity of an optical probe beam that passes through the crystal. The ellipticity modulation of the optical beam can then be polarization analyzed to provide information on the amplitude of the applied electric field. A balanced detection system analyzes a polarization change from the electro-optic crystal and correlates it with the amplitude of the THz electric field. A variable time delay between the THz radiation pulse and the optical probe pulse is typically provided by changing the relative length of the beam path between the THz radiation pulse and the optical probe pulse. This technique is sometimes referred to as a "pump-probe" sampling method. FS-EOS gives a signal directly proportional to the THz electric field. Because the EO effect is almost instantaneous on the THz time scale, the detection bandwidth is much higher than that of a PDA.

In FS-EOS, the choice of sensor crystals is determined by the matching between the phase velocity of the THz wave and the group velocity of the ultrafast probe pulse. A preferred optical source for the generation of THz waves is an ultrafast Ti:sapphire laser that has an average power of about 0.5 W, a pulse duration of about 100 fs, and a center wavelength of about 800 nm. For a THz-TDS system using a common Ti:sapphire ultrafast laser, zinc telluride (ZnTe) is a preferred sensor crystal for EO sampling, because the velocity-matching condition is well satisfied in ZnTe at an optical wavelength of 822 nm, which also makes ZnTe a preferred electro-optic crystal for THz optical rectification generation. A preferred orientation to generate and detect THz waves in a ZnTe crystal is a <110> cut. If optical sources with different wavelengths are used, the phase matching condition may be different, meaning that other electro-optical crystals may be more favorable. For example, GaAs is more favorable for an 1.5 $\mu$m optical beam and InP is more favorable for an 1.3 $\mu$m optical beam.

According to Abbe's law, the spatial resolution that can be achieved when imaging with electromagnetic waves is limited by the wavelength of the employed radiation. The diffraction limit to spatial resolution is not fundamental, however, but rather arises from the assumption that the light source is typically many wavelengths away from the sample of interest. With the lateral scanning of a light source in close proximity to a sample, one can generate an image at a resolution that is functionally dependent on only the source size and the source-to-sample separation, each of which can, in principle, be made much smaller than the wavelength of the employed radiation.

Conventionally, in near-field microscopy, the light incident upon one side of an optically opaque screen is transmitted through a subwavelength-diameter aperture to realize a tiny source. Near-field microwave and optical microscopy is already well known. The concept of near-field microscopy has also been adopted to improve upon the diffraction-limited spatial resolution of scanning THz wave imaging systems, in which the peak frequency of THz radiation is generally 0.5 THz. One near-field method is to use a THz source comprising a tapered metal tube with a nearly circular aperture of less than 100 $\mu$m diameter. Another near-field method is to place the sample that is to be imaged close to the THz emitter. One disadvantage of the tapered metal tube is, however, that the high-pass filtering of the THz signal due to the waveguide effect of the tapered metal tube not only decreases the THz signal, but also seriously limits the transmitted THz bandwidth. Another disadvantage is that the spatial resolution is determined by the spot size of the optical pump beam and the finite thickness of the electro-optic crystals needed for relatively strong THz generation. If the spot size of the optical beam is too small, two-photon absorption may limit the generation efficiency through the saturation effect.

Consequently, there is still a need in the art for methods of and systems for improving the spatial resolution of THz imaging that avoid some of the disadvantages of currently used systems.

SUMMARY OF THE INVENTION

One aspect of the invention comprises a system for using terahertz (THz) radiation to produce an image of an object. The system comprises a mechanism for providing an optical pump pulse, an optical probe pulse, and an optical gating pulse with a variable delay time between the optical pump pulse and the optical probe pulse. The system also comprises a THz emitter for emitting a beam of THz radiation when activated by the optical pump pulse, and a mechanism for chopping the optical gating pulse on and off. The system also comprises a layer of semiconductive material that is either part of the object itself or a discrete layer between the object and the THz beam. The system further includes structure for focusing the optical gating pulse and the THz beam on the layer of semiconductive material so that the gating pulse illuminates a gating pulse focal spot on the layer of semiconductive material. The gating pulse focal spot has a diameter effective to cause measurable modulation in transmission of the THz beam through the layer of semiconductive material when the gating pulse is on as compared to when the gating pulse is off, creating alternating modulated THz beams that illuminate the object.

A THz receiver, positioned to receive the alternating modulated THz beams after reflection from or transmission through the object, modulates the optical probe pulse with the alternating modulated THz beams to create corresponding modulation in the polarization ellipticity of the optical probe pulse. An element converts the modulation in the polarization ellipticity of the optical probe pulses to intensity modulation. Another element converts the intensity modulation to electronic information. Still another element receives the electronic information and produces an image of the object from the electronic information.

The THz emitter and the THz receiver may each comprise an electro-optic crystal or a photoconductive antenna. The mechanism for providing the optical pump pulse, optical probe pulse, and optical gating pulse may comprise a laser source. One delay stage may be used to provide a variable delay time between the optical pump pulse and the optical probe pulse, and another delay stage may be used to provide a variable delay time between the optical gating pulse and the optical pump pulse. A chopper may be used to turn the optical gating pulse on and off. A lens may be used to focus the optical gating pulse on the object.

Another aspect of the invention includes a method for using THz radiation to generate an image of an object. The method comprises providing an optical pump pulse, an optical probe pulse, and an optical gating pulse with a variable delay time between the optical pump pulse and the optical probe pulse. The method further comprises activating a THz emitter with the optical pump pulse to emit a beam of THz radiation, and chopping the optical gating pulse on and off. The optical gating pulse and the THz beam are focused on a layer comprising semiconductive material that is part of the object itself or a discrete layer placed between the object and the THz beam, so that the gating pulse illuminates a gating pulse focal spot on the layer comprising semiconductive material.

The gating pulse focal spot has a diameter effective to cause measurable modulation in transmission of the THz beam through the layer comprising semiconductive material when the gating pulse is on as compared to when the gating pulse is off, creating alternating modulated THz beams which illuminate the object. The optical probe pulse is modulated with the alternating modulated THz beams in a THz receiver, positioned to receive the alternating modulated THz beams reflected from or transmitted through the object, to create corresponding modulation in the polarization ellipticity of the optical probe pulse. The modulation in polarization ellipticity of the optical probe pulse is converted to an intensity modulation, which is detected and converted to electronic information. The electronic information is then received and processed to produce the image of the object.

The measurable modulation in transmission of the THz beam through the semiconductor may be caused by generation of photocarriers within the semiconductor, particularly where the semiconductor comprises gallium arsenide. The measurable modulation in transmission of the THz beam through the semiconductor may also be caused by a temperature effect within the semiconductor, particularly where the semiconductor comprises silicon.

Another aspect of the invention includes a method of improving spatial resolution of a pump-probe THz imaging system to produce an image of an object comprising a semiconductive material. The improvement comprises the step of providing a chopped optical gating beam focused on the object in a gating pulse focal spot, the gating pulse focal spot having a diameter effective to cause measurable modulation in transmission of a THz beam through the object when the gating pulse is on as compared to when the gating pulse is off, creating alternating modulated THz beams for detection and processing.

Yet another aspect of the invention includes a method of improving spatial resolution of a pump-probe THz imaging system to produce an image of an object using a THz beam. The improvement comprises the steps of (a) placing a layer of semiconductive material between the object and the THz beam, and (b) providing a chopped optical gating beam focused on the layer of semiconductive material in a gating pulse focal spot. The gating pulse focal spot has a diameter effective to cause measurable modulation in transmission of the THz beam through the layer of semiconductive material when the gating pulse is on as compared to when the gating pulse is off, creating alternating modulated THz beams for detection and processing.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 11 shows an exemplary reflection mode system having a dynamic aperture and a transceiver for the THz transmitter and receiver; and FIG. 12 shows a portion of an exemplary system in either reflection or transmission mode, illustrating the use of a layer of semiconductive material between the THz beam and the object to be imaged.

DETAILED DESCRIPTION OF INVENTION

The exemplary near-field THz wave imaging method of the present invention uses a dynamic aperture rather than a physical aperture. The near-field THz aperture is provided by a transient photocarrier layer or temperature effect (or both) in a semiconductor induced by an optical gating beam. The gating beam modulates the transmission of the THz beam through the semiconductor. The size of the photocarrier layer is determined by the focal size of the optical beam, which can be as small as several microns, and can be easily adjusted by moving the focusing lens. The thickness of the photo-carrier layer is determined by the absorption depth of the optical beam on the semiconductor material, which is generally on the order of several microns. Therefore, the high-pass filtering of the THz signal due to the waveguide effect can be avoided and the transmitted THz bandwidth can be maintained, which is important for THz-TDS on a micrometer scale.

Figure 1:
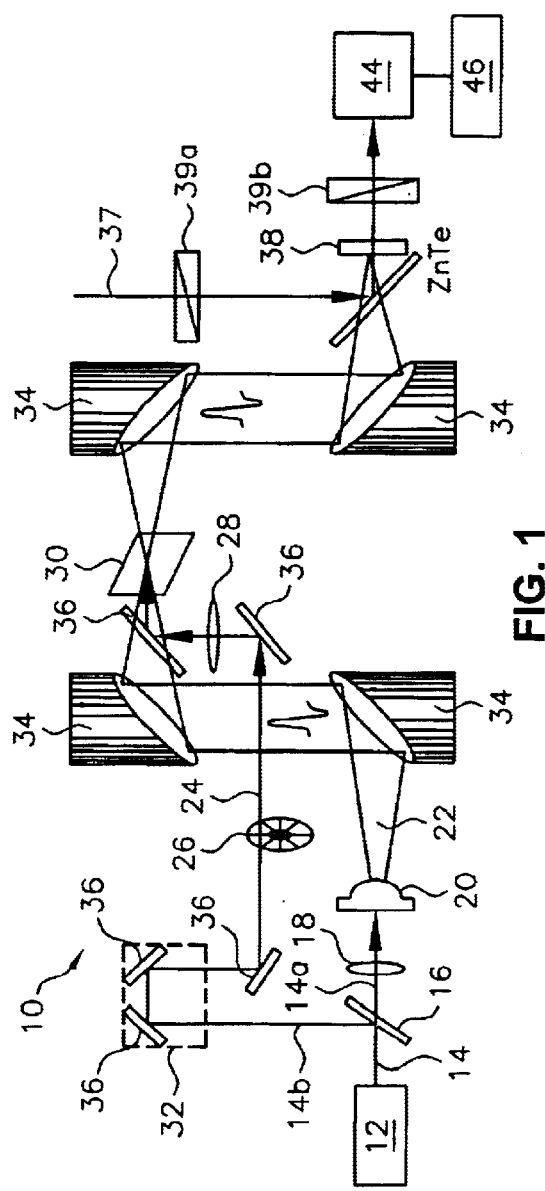
FIG. 1 is a schematic illustration of an exemplary transmission mode system comprising a dynamic aperture.

Referring now to FIG. 1, there is shown a schematic illustration of a near-field THz wave imaging system 10 in a transmission geometry having a dynamic aperture. A laser source 12 may be any laser source known in the art, such as a regeneratively amplified Ti:sapphire laser (Coherent RegA 9000). Laser source 12 repeatedly produces a pulse 14, which in an exemplary embodiment may have an 830 nm wavelength for a duration of 250 fs and may be repeated at a rate of 250 kHz, providing a pulse energy of 2 $\mu$J. Pulse 14 is split into pulses 14a and 14b by a splitter 16. Pulse 14a is focused by a lens 18 onto a THz emitter 20, typically an EO crystal, which generates a THz beam 22. For example, a 2 mm-thick (110) ZnTe crystal generates a THz beam with a peak at 0.9 THz when excited by the pump optical beam having the characteristics described above.

Figure 2:
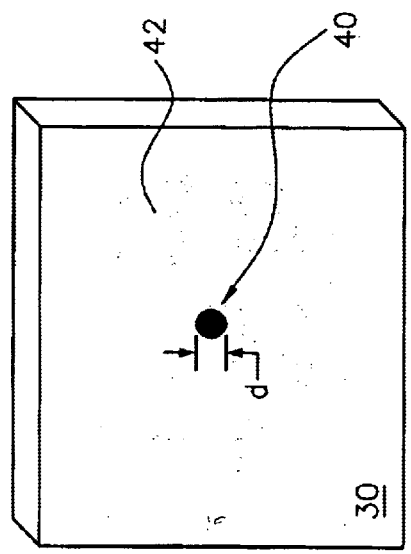
FIG. 2 is a schematic illustration of a preferred relationship between the gating beam focal spot and the THz beam focal spot.

A distinguishing difference between system 10 and a conventional THz wave imaging system is the introduction of an optical gating beam 24, created by chopping laser pulse 14b with a chopper 26. In the embodiment shown in FIG. 1, gating beam 24 is focused by a lens 28, for example a lens having a focal length (f) of 7.6 cm, onto a semiconductor wafer 30 along with THz beam 22. FIG. 2 shows a comparison of the focal spot 40 of gating beam 24, having a diameter d, as compared to the focal spot 42 of THz beam 22 on semiconductor wafer 30. Preferred materials for semiconductor wafer 30 include but are not limited to silicon or gallium arsenide (GaAs), including low-temperature (LT) GaAs. Chopper 26 alternates optical gating beam 24 on and off at semiconductor wafer 30, thus providing alternating modulated THz beams transmitted through semiconductor wafer 30.

After passing through semiconductor wafer 30, the alternating modulated THz beam is then directed to a THz detector 38, such as an EO crystal, where the alternating modulated THz beam modulates the elliptical polarization of the probe pulse 37. Probe pulse 37 typically comprises a pulse split from laser pulse 14 and sent through a delay stage (not shown), as is well known in the art. A polarizer 39a polarizes the probe light for optimal EO detection configuration, as is well known in the art. Another polarizer 39b transfers the phase variation in the probe pulse induced by the THz pulse to an intensity variation that can be detected by a detection mechanism 44 known in the art, such as a photodetector. The detected intensity variation is converted to electronic information by detection mechanism 44. A computer 46 or other processor then stores and processes the electronic information to produce an image of the object.

A mechanical delay stage 32 is also illustrated in FIG. 1. It should be noted that, although schematically shown with a number of parabolic mirrors 34 for reflecting THz beams and combination mirrors-beam splitters 36 for reflecting the optical beams, such elements are shown merely to direct the representations of the beams in the schematic diagram. The actual system 10 may have greater or fewer mirrors and beam splitters as needed to manipulate the beam as necessary to meet any physical constraints. It should also be understood that although lens 28 and polarizers 39a and 39b are shown, additional polarizers, lenses, or other optical elements may be provided as are known in the art for THz systems generally.

In addition, the portion of the system 10 after semiconductor wafer 30 is not limited only to the configuration depicted in FIG. 1. Rather, system 10 may comprise any configuration known in the art for detecting a THz signal. Also, although shown in a preferred embodiment in which THz emitter 20 and THz detector 38 comprise EO crystals, photoconductive antennas may also be used for the THz detector 38 and THz emitter 20.

Furthermore, the dynamic aperture of the present invention may also be used with a THz transceiver, such as the transceiver described in U.S. patent application Ser. No. 09/826,458 filed on behalf of inventors Zhang et al. and published as publication number US-2001-0038074-A1, incorporated in this document by reference. Such an application is typically used in a reflection-mode as shown in the exemplary system illustrated in FIG. 11. The main components of the system shown in FIG. 11 are similar to those shown in FIG. 1, and thus are numbered the same.

FIG. 11 shows the delay stage 1101 (often referred to as a Michelson interferometer) comprising the moving stage 1102 and related optics (splitters and mirrors 36a–f) for creating a temporal offset between optical probe pulse 37 and optical pump pulse 14b going into the transceiver 1100. As pump pulse 14b is converted to THz beam 22 and reflected from an object such as semiconductor wafer 30, the reflected THz beam returns to transceiver 1100 at the same time as probe pulse 37 hits transceiver 1100, thereby causing the characteristic modulation of optical probe pulse 37, a portion of which is reflected by transceiver 1100. The reflected portion 1106 of optical probe pulse 37 then travels to polarizer 39b, detection mechanism 44, and processor 46, which operate similarly to the like elements in the transmission mode geometry shown in FIG. 1. Unlike the transmission mode geometry, the reflected mode geometry used with THz transceiver 1100 allows imaging of objects that are not transmissive of THz radiation.

FIG. 12 illustrates another aspect of the invention that may be used in a reflected or transmitted geometry. The object 1200 may have between it and the THz beam, prefereably on its surface, a thin layer 1202 of semiconductive material. Thin layer 1202 of semiconductive material provides the dynamic aperture, allowing use of the method and system for imaging objects, such as object 1200, that are not semiconductive. Semiconductive thin layer 1202 may also be used in conjunction with a sermiconductive object, if desired for a particular imaging application. Thin layer 1202 of semiconductive material is larger than but close to the optical beam absorption depth of the semiconductor. For example, the optical beam absorption depth in GaAs is approximately 1 $\mu$m, so thin layer 1202 is preferably larger than 1 $\mu$m and more preferably in a range of 1.5–3 $\mu$m thick. Thus, both systems for imaging semiconductive objects such as object 30 shown in FIGS. 1 and 11, and applications for imaging objects (semiconductive or non-semiconductive) using a discrete semiconductive material thin layer 1202 can be said to comprise a layer of semiconductive material. In the first instance, the layer is part of the object, whereas in the second instance the layer is placed between the THz beam and the object.

In an exemplary embodiment, the average power of the optical pulses comprising gating beam 24 may be approximately 12 mW. The arrival time of those pulses at semiconductor wafer 30 may be independently controlled by mechanical delay stage 32. Mechanical delay stage 32 is shown in both FIG. 1 and FIG. 11.

In a typical optical pump and THz probe system, the THz beam is chopped, and the transmission of the THz beam through the sample shows a step-function-like variation with the time delay between the THz and optical pump beams. Such a variation of the THz wave transmission is not quite discernable when the optical beam is tightly focused on a semiconductor wafer, however, because the effective modulation area is too small to cause significant modulation of the THz wave transmission. By chopping optical gating beam 24 instead of THz beam 22, a step-function-like variation of the THz wave transmission is achieved with greatly improved sensitivity.

Figure 3:
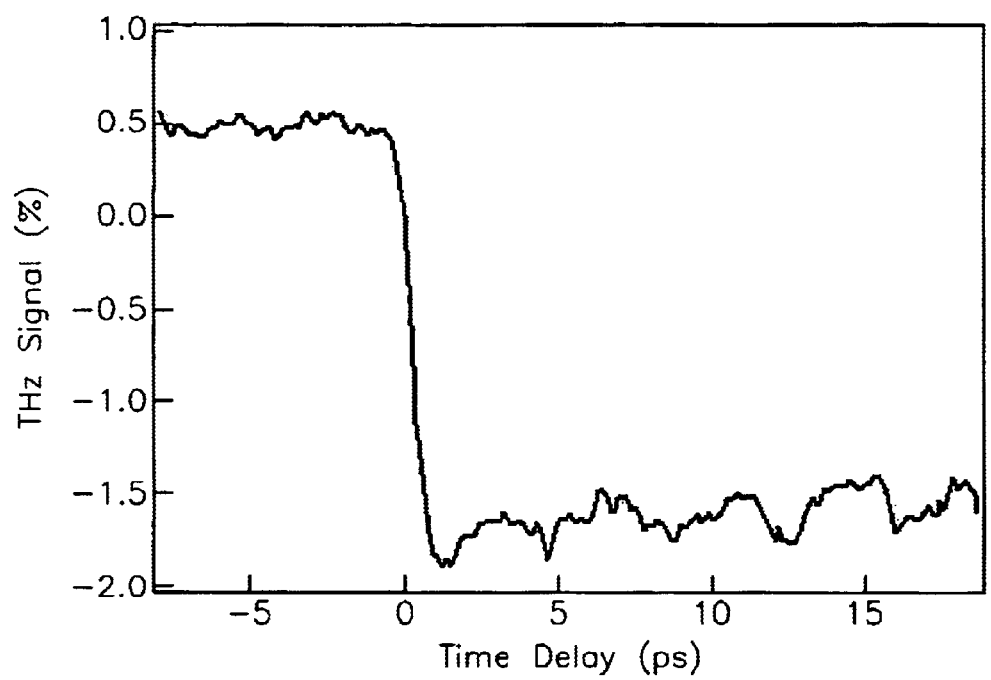
FIG. 3 is a graph of time delay in picoseconds between the THz pulse and the gating pulse versus the percentage of transmitted THz signal intensity as compared to that detected by chopping the optical pump beam for a gating beam size of 22 $\mu$m.

FIG. 3 shows the variation of the THz signal transmitted through a GaAs wafer with the time delay between the THz pulse and the gating pulse for a gating beam focal diameter estimated to be about 22 μm at the GaAs wafer. It should be noted that all of the optical gating beam sizes estimated in this document are based on a scanning measurement of a razor blade. The measured THz signal is proportional to the fluctuation of the THz wave transmission during the "on" and "off" states of the optical gating beam chopped by the mechanical chopper. When the optical gating pulse arrives at the GaAs wafer earlier than the THz pulse, it is believed that the generation of photocarriers increases the local conductivity of the GaAs wafer and decreases the THz wave transmission in an area determined by the size of focal spot 40 of optical gating beam 24, as shown in FIG. 2. The decrease of THz transmission due to the increase of local conductivity can last for a time scale of 100 ps until the electron and holes diffuse into the sample and eventually recombine.

The spatial resolution that can be achieved using a dynamic aperture is determined by the focal size d of optical gating beam 24. The system signal-to-noise ratio (SNR) is also a factor. A decrease in the spot size of gating beam 24 on the sample increases the spatial resolution, but it also decreases the modulation of THz beam 22, thereby degrading the SNR. Thus, there is a tradeoff between the image resolution and SNR.

In addition to the above considerations, the laser fluence of optical gating beam 24 on semiconductor wafer 30 should be smaller than the ablation threshold of the semiconductor (approximately 175 mJ/cm$^2$ for GaAs). Also, temperature effects, as detailed in Example 2 below, may need to be considered when using a dynamic aperture method on silicon.

The invention will next be illustrated by reference to a number of examples. The examples are included to more clearly demonstrate the overall nature of the invention. These examples are exemplary, not restrictive, of the invention.

EXAMPLE 1

Figure 4A:
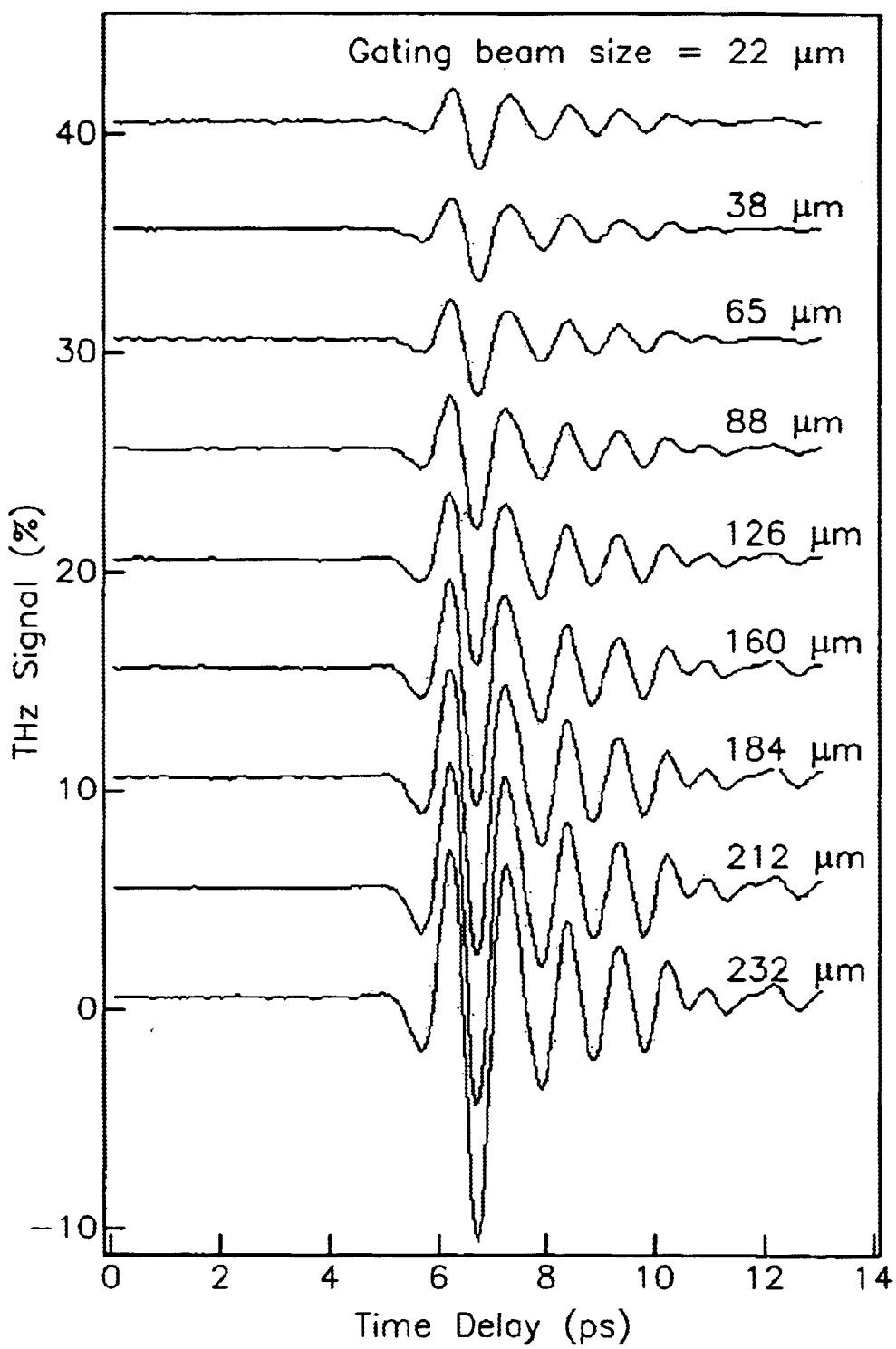
FIG. 4A is a graph of the time delay in picoseconds between the THz pump and probe beam versus the percentage of transmitted THz signal through a GaAs wafer for a plurality of gating beam focal spot sizes, with a vertical shift in the data provided for clarity of presentation.
Figure 4B:
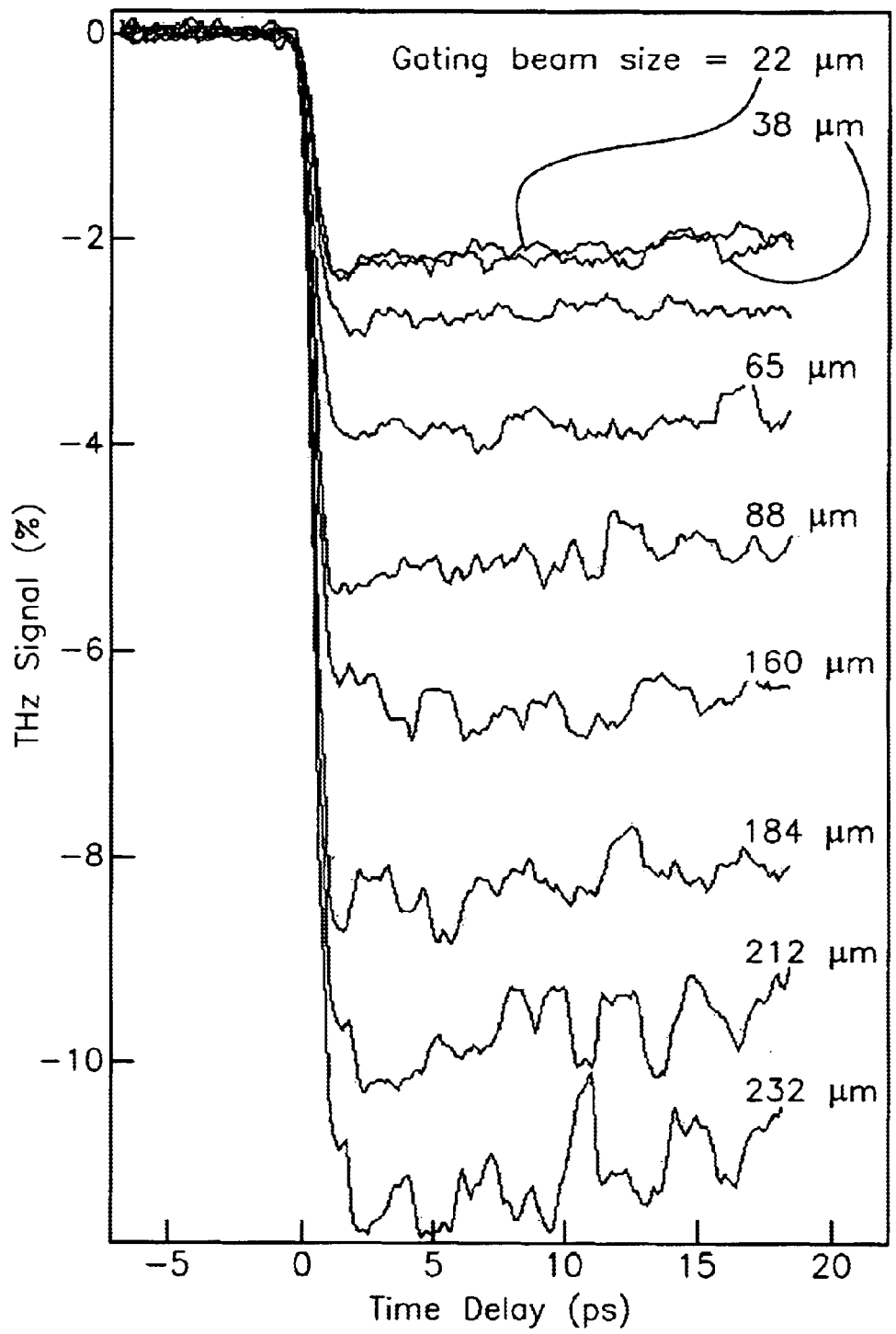
FIG. 4B is a graph of the time delay in picoseconds between the THz beam and the gating pulse versus the percentage of transmitted THz signal for a plurality of gating beam focal spot sizes.

FIGS. 4A and 4B show how the size of gating beam 24 affects the THz signal level. To generate the graphs shown in FIGS. 4A and 4B, the gating beam size was changed by moving the gating beam focusing lens 28 (shown in FIG. 1) along the beam propagation direction at a step size of 1 mm to achieve optical gating beam diameters d of approximately 22 μm, 38 μm, 65 μm, 88 μm, 126 μm, 160 μm, 184 μm, 212 μm, and 232 μm, respectively. A semi-insulating GaAs wafer having a resistivity of approximately $2\times10^8$ Ωcm was used as the gating material for a gating beam having a power of about 12 mW. FIG. 4A shows the THz waveforms generated during this procedure by varying the delay between the pump pulse and probe pulse. A vertical shift in the data is made for clarity.

To illustrate the modulation effect of photocarriers on THz pulses, a corresponding set of data was also recorded by changing the time delay between the THz and optical gating beams, as shown in FIG. 4B. Negative time delay means that the optical gating pulse arrives later than the THz pulse. The absolute THz signal in FIG. 4B is expressed in terms of a percentage of the peak amplitude of the original THz waveform, namely the THz pulse transmitted through the GaAs wafer measured by chopping the THz pump beam. It is seen that, when the gating beam size is 22 μm, the peak amplitude of the THz waveform decreases to about 2%. The THz signals after the zero time point in FIG. 4B indicate the modulation of photocarriers on THz wave transmission.

Figure 4C:
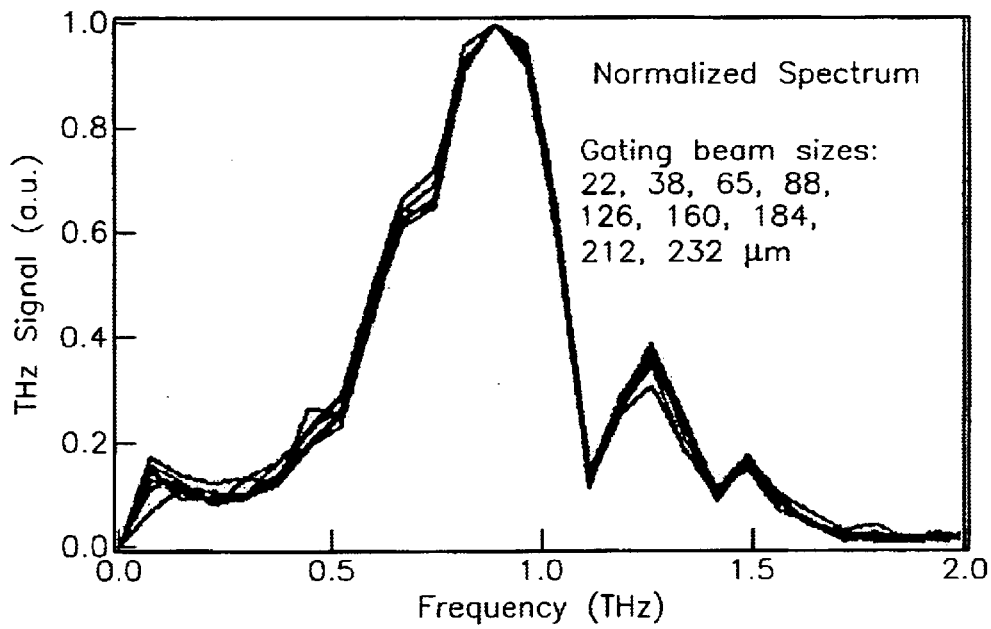
FIG. 4C is a graph of the normalized fast Fourier transforms of the THz time domain waveforms detected at various gating beam focal spot sizes.

The Fourier transforms of the set of THz waveforms are normalized and shown in FIG. 4C. The result clearly shows that the dynamic aperture technique is free of the spatial filter effect, because the thickness of the photocarrier layer on a GaAs wafer is on the order of 1 μm. Thus, one advantage of the method of the present invention for improving spatial resolution is that the THz bandwidth can still be maintained.

Figure 5:
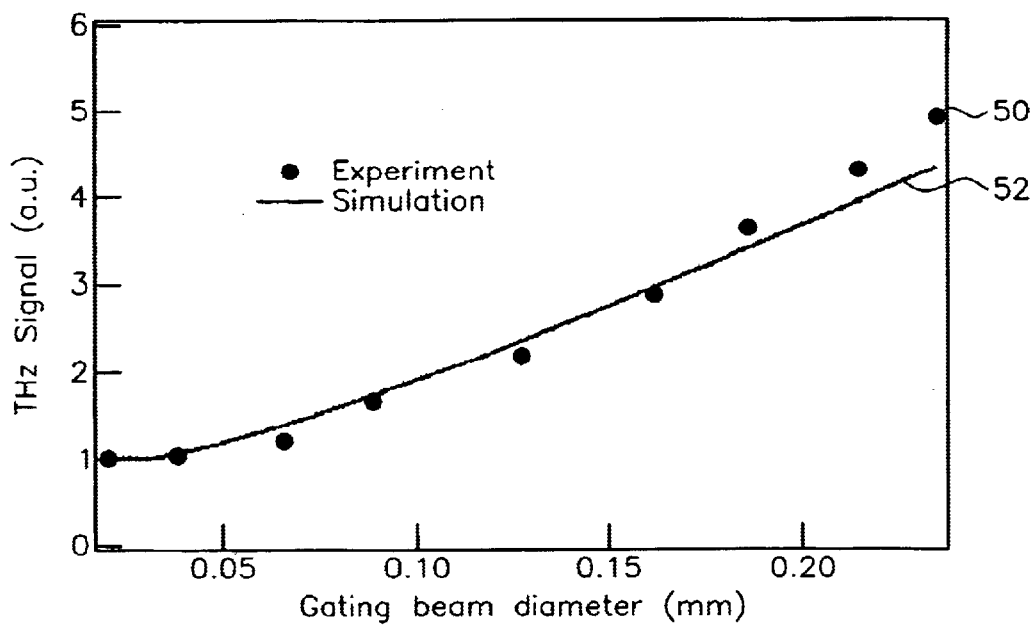
FIG. 5 is a graph of the gating beam diameter in millimeters versus the THz signal in arbitrary units as determined by experiment and by simulation.

FIG. 5 illustrates how the amplitude of the peak frequency (0.9 THz) varies with the nine different gating beam sizes (the experimental data points are shown by filled circles 50). It is believed that both the size of the optical gating beam and the conductivity of the local photocarrier layer affect the magnitude of the THz signal. A simulation taking into account these two factors and based on classical aperture diffraction theory, the Drude model, and the Fresnel formula was used to calculate the conductivity of the local photocarrier layer and the THz transmission. The results are plotted as the line 52 in FIG. 5. As shown in FIG. 5, the simulation fits the experimental data well.

EXAMPLE 2

Figure 6A:
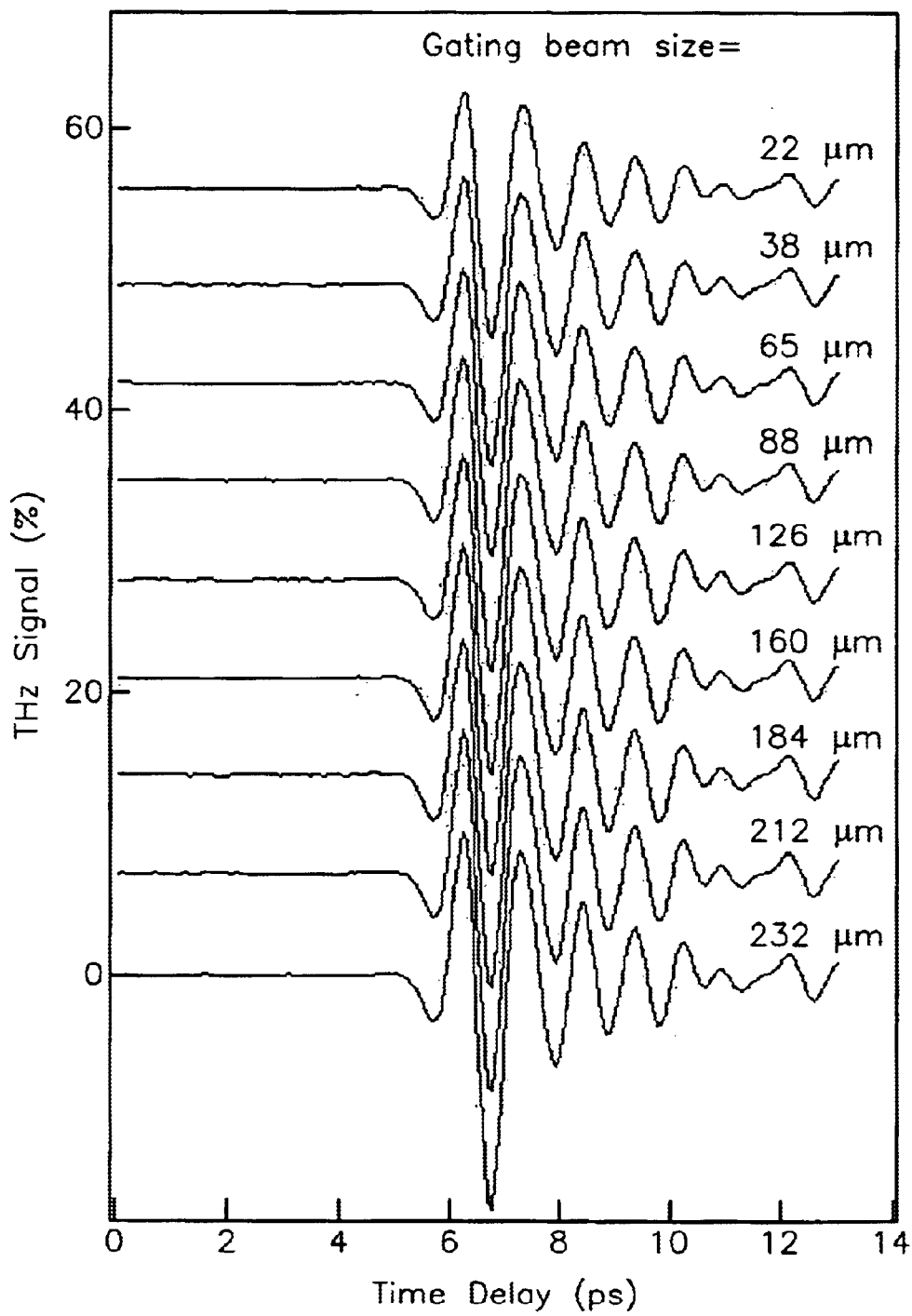
FIG. 6A is a graph of the time delay in picoseconds between the THz pump and probe beam versus the percentage of transmitted THz signal through an n-doped silicon wafer for a plurality of gating beam focal spot sizes, with a vertical shift in the data provided for clarity of presentation.
Figure 6B:
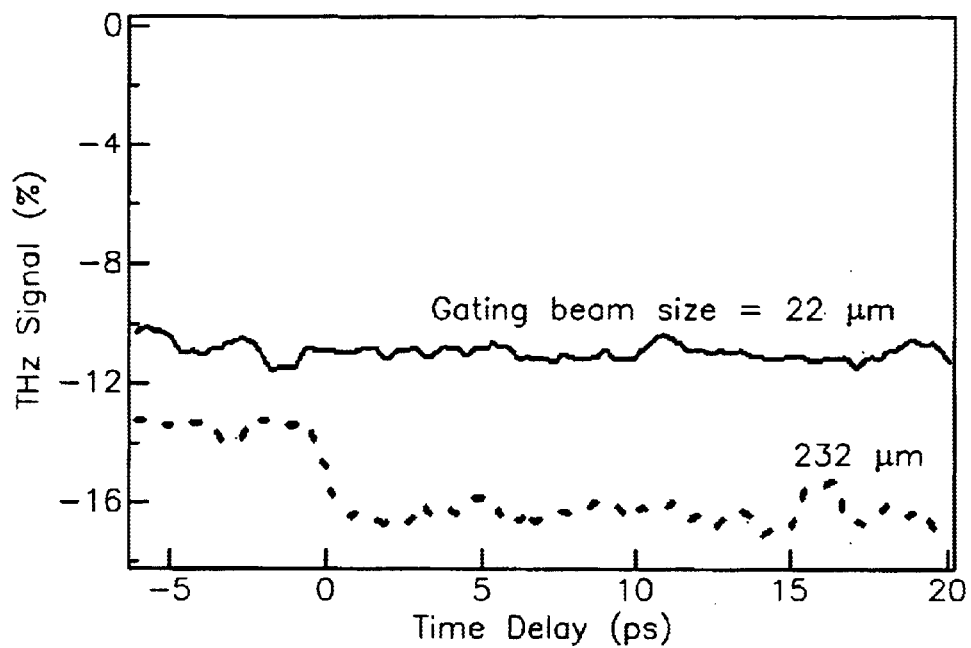
FIG. 6B shows a graph of the time delay in picoseconds between the THz beam and the optical gating beam versus percentage of THz signal transmitted through an n-doped silicon wafer for a gating beam focal spot size of 22 $\mu$m as compared to a gating beam focal spot size of 232 $\mu$m, for a gating power of 13 mW and a laser repetition rate of 250 kHz.

Referring now to FIG. 6A, there is shown a set of THz waveforms similar to those in FIG. 4A. The waveforms of FIG. 6A were measured on an n-doped silicon wafer, with a resistivity of approximately 4.5 Ωcm, using a laser repetition rate of 250 KHz and a gating power of 13 mW. The decrease of the THz signal with the gating beam sizes does not follow the same trend as that shown in FIG. 4A. The signal is almost saturated after the gating beam diameter has decreased to 126 μm. FIG. 6B shows the experimental result of changing the time delay between the THz and optical gating beams. The absence of the step-function-like variation of the THz signal for a gating beam diameter of 22 μm in silicon is noticeable compared to the same measurement on a GaAs wafer as shown in FIG. 4A. Even when the gating beam arrives later than the THz beam, some of the THz signals in FIG. 6A have a signal magnitude about 4 times larger than that of GaAs.

These experimental phenomena are believed to be attributable to the local temperature increase induced by the previous gating pulses. The local temperature increase is believed to change the complex refractive index of silicon, especially the imaginary part. Such a temperature effect can last as long as several milliseconds in silicon. Because the repetition rate of the laser used in the experiment was just 250 kHz, the temperature effect can still influence the THz wave transmission even when the gating beam arrives later than the THz beam on the silicon wafer. When the gating beam arrives at the sample earlier than the THz beam, the absence of the photocarrier modulation on the THz beam is believed to be due to the small area of the local photocarrier layer, which can modulate only a small portion of the transmitted THz radiation. The modulation effect of the photocarrier is thus buried in the fluctuation of the THz signal caused by the temperature effect. By increasing the gating beam diameter on the sample to 232 μm, as shown in FIG. 6B, the modulation of the THz beam by the photocarriers can be observed, because the larger gating beam diameter corresponds to less light intensity and less temperature increase, but larger THz modulation by the photocarriers.

Figure 6C:
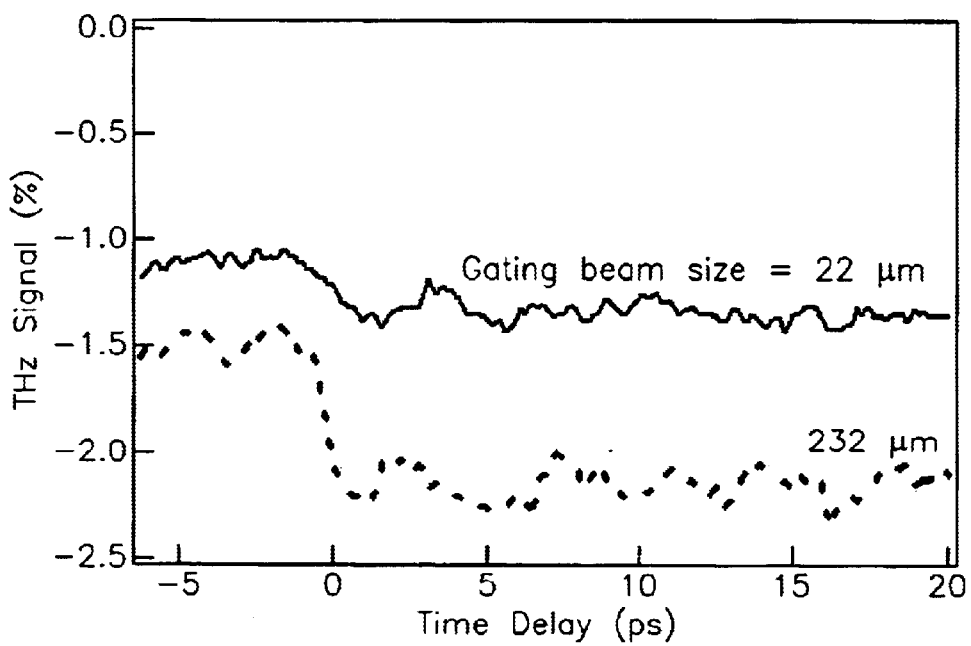
FIG. 6C shows a graph of the time delay in picoseconds between the THz beam and the optical gating beam versus percentage of THz signal transmitted through an n-doped silicon wafer for a gating beam focal spot size of 22 $\mu$m as compared to a gating beam focal spot size of 232 $\mu$m, for a gating power of 1.8 mW and a laser repetition rate of 250 kHz.
Figure 6D:
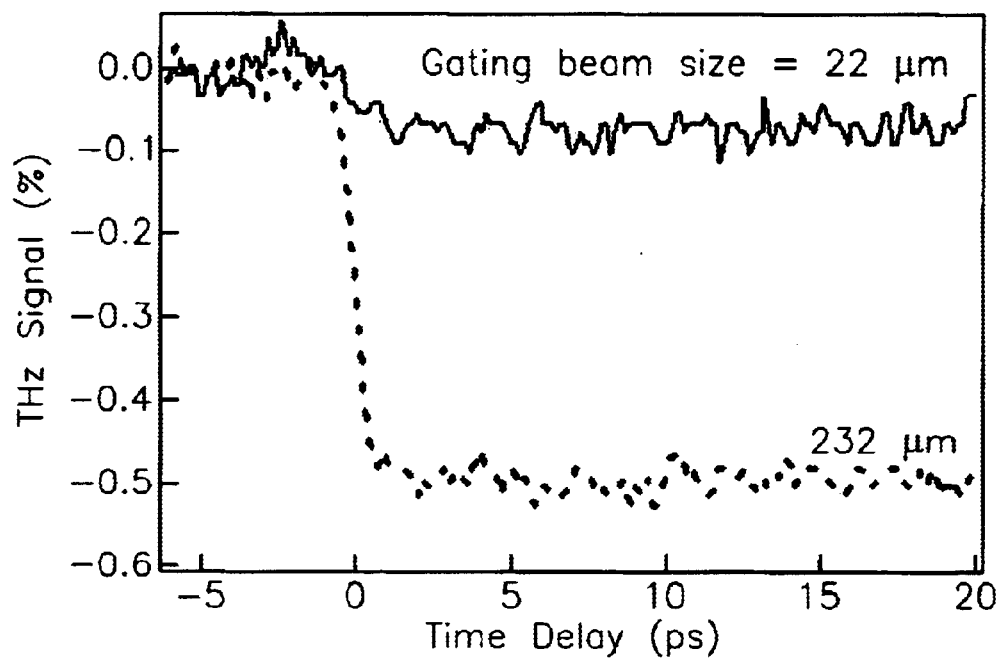
FIG. 6D shows a graph of the time delay in picoseconds between the THz beam and the optical gating beam versus percentage of THz signal transmitted through an n-doped silicon wafer for a gating beam focal spot size of 22 $\mu$m as compared to a gating beam focal spot size of 232 $\mu$m, for a gating power of 1.8 mW and a laser repetition rate of 10 kHz.

The local temperature increase of a silicon wafer by the incidence of an optical beam is proportional to the light intensity. Therefore, the THz signal modulated by the temperature effect decreases when the gating beam power decreases, as shown in FIG. 6C. To generate the signals plotted in FIG. 6C, the gating beam power was reduced to 1.8 mW. In FIG. 6C, the THz signal modulated by the photocarriers can be observed when the gating beam size is 22 μm. By decreasing the laser repetition rate to 10 kHz, while maintaining the gating power, the experimental result shown in FIG. 6D shows that the measured THz signal was mainly due to modulation of the photocarrier layer.

The above results indicate that, although the present method is also applicable to a silicon wafer, the spatial resolution of a THz wave imaging system with a dynamic aperture created on a silicon wafer is limited. In principle, if the modulation of the THz signal were due only to the photocarrier layer, the spatial resolution would be uniquely determined by the diameter of the photocarrier layer or the gating beam size on the semiconductor wafer. For a silicon wafer, however, the temperature effect actually damages the spatial resolution, because the detected THz signal at a small focal size of the gating beam is mainly from the temperature modulation and is proportional to the heated area. The size of the heated area can be much larger than that of the photocarrier layer, due to the heat diffusion and the relatively long lifetime of the temperature effect.

EXAMPLE 3

Figure 7A:
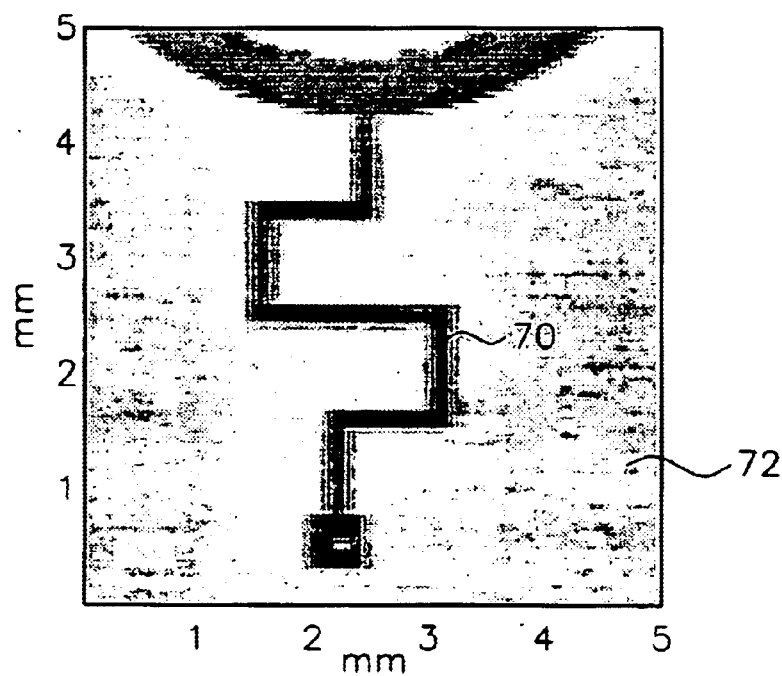
FIG. 7A shows an image of a metal line on a silicon wafer produced using a dynamic aperture THz imaging method of the present invention.

When the optical gating beam is incident on a metal line deposited on the semiconductor wafer, there is no THz wave transmission through the metal. FIG. 7A shows a THz wave image obtained by using a dynamic aperture method as described above to image a simple metal circuit 70 deposited on a semi-insulating GaAs wafer 72 having a thickness of about 0.4 mm. To generate this image, the optical gating pulse was focused using lens 28 (shown in FIG. 1) having f=15 cm and a focused spot size of about 50 μm. The timing was set so that the optical gating beam 24 arrived at the sample several picoseconds earlier than the THz beam 22. For comparison, circuit 70 was also imaged by the conventional THz wave imaging technique in which the optical gating beam was blocked and the THz optical pump beam was modulated by a chopper. That image is shown as FIG. 7B.

Figure 7B:
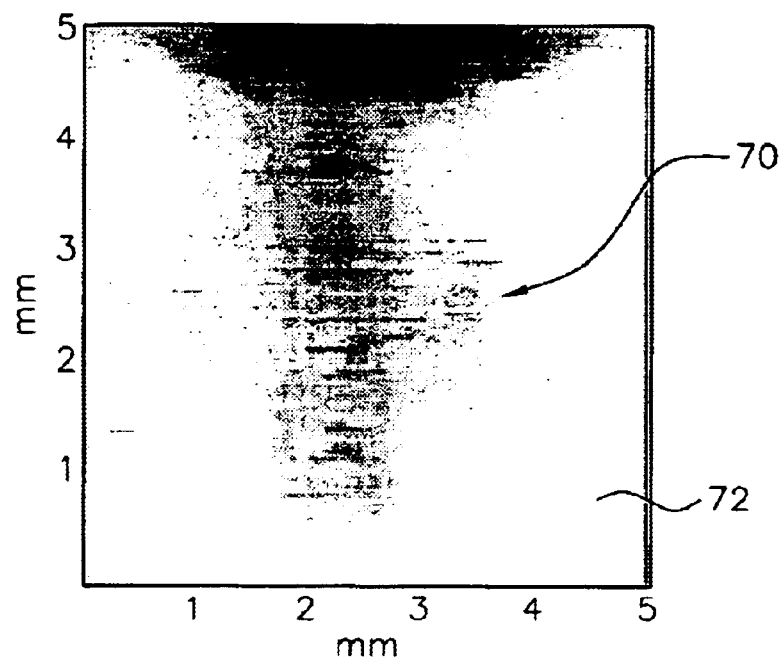
FIG. 7B shows an image of the metal line of FIG. 7A produced using a THz imaging technique of the prior art.

A comparison of FIGS. 7A and 7B clearly shows how the spatial resolution and image contrast are greatly improved by the introduction of a dynamic aperture. The transient photocarrier layer, excited by optical gating beam 24, serves as a near-field aperture, which partially blocks the THz wave transmission in a region with a size much smaller than the focal spot of THz beam 22. Because the dynamic aperture and metal circuit 70 are directly on the front surface of the sample, namely wafer 72, THz propagation is not involved and the spatial resolution of the THz wave image is thus solely determined by the focal size of optical gating beam 24.

Figure 7C:
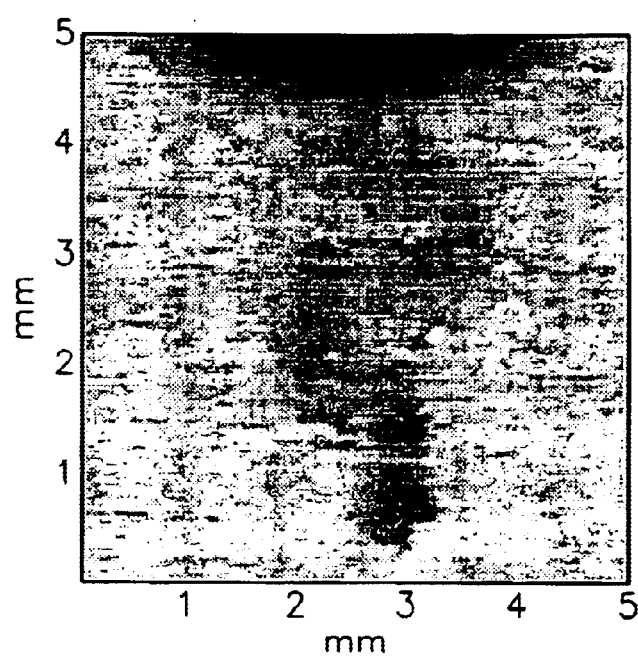
FIG. 7C shows an image of the metal line of FIG. 7A produced using the dynamic aperture THz imaging method, with the wafer reversed.

To test the effect of THz propagation, the circuit sample was flipped and a THz image of circuit 70 on the backside of wafer 72 was obtained. The results are shown in FIG. 7C. Because THz beam 22 propagated a distance of about 0.4 mm (the thickness of wafer 72) to reach the pattern, the spatial resolution and contrast were relatively reduced, clearly showing a diffraction effect.

EXAMPLE 4

Figure 8A:
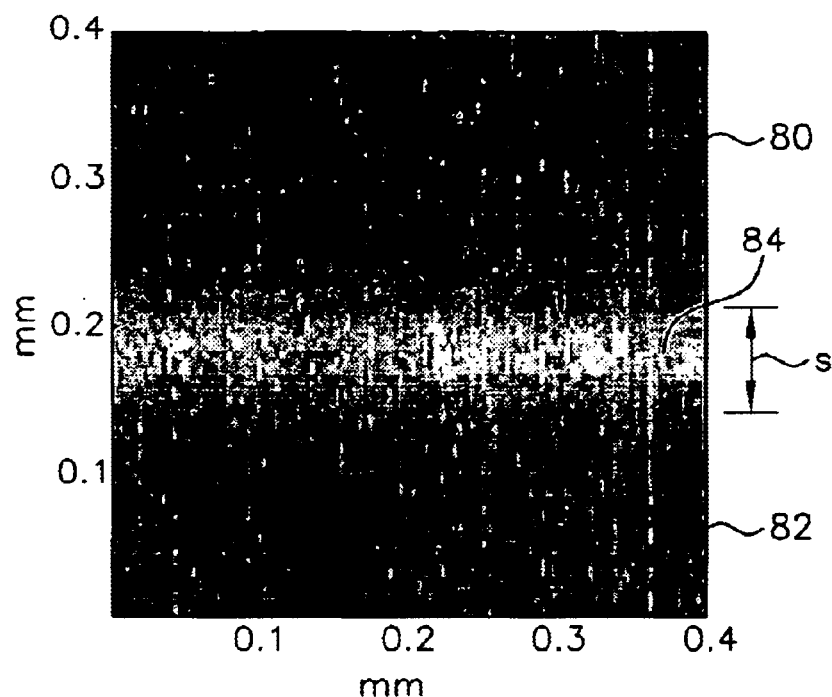
FIG. 8A shows an image of a pattern of two metal films deposited on a LT-GaAs wafer imaged using a dynamic aperture THz imaging method of the present invention.
Figure 8B:
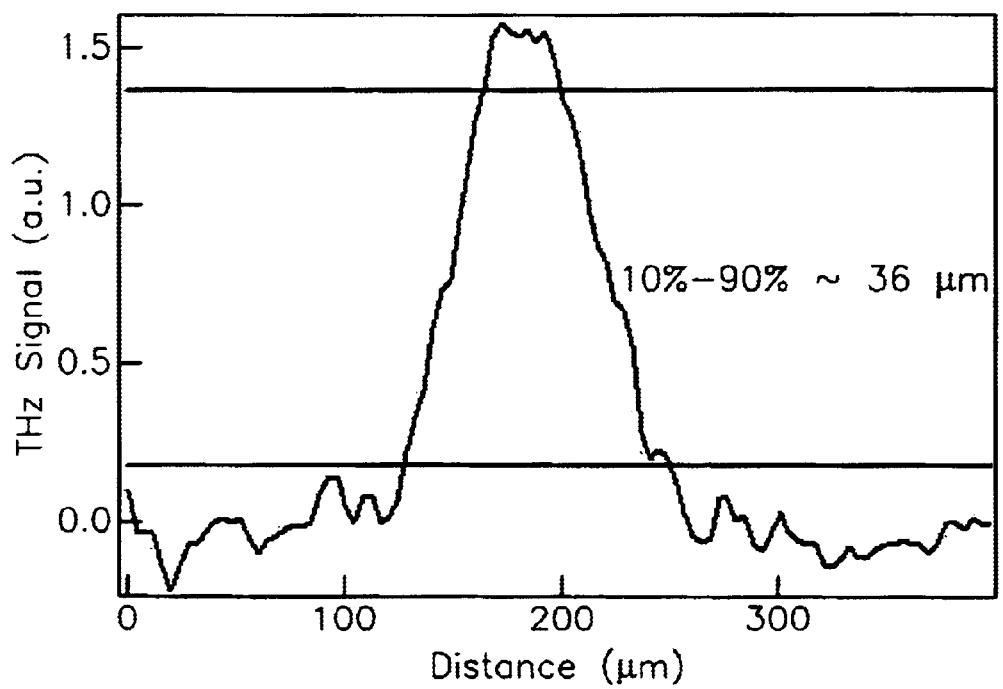
FIG. 8B shows a waveform for the pattern imaged in FIG. 8A, graphed as distance in micrometers versus the THz signal in absolute units.

To quantitatively estimate the spatial resolution of the THz wave imaging system with a dynamic aperture, a simple metal pattern, comprising two metal films 80 and 82, deposited on an LT-GaAs wafer 84, was imaged. The results are shown in FIG. 8A. The separation (s) between metal films 80 and 82 was approximately 50 μm. The optical gating pulse was focused by a lens with f=7.6 cm, and its focused spot size was 22 μm. As shown in FIG. 8B, from the distance between 90% and 10% of the maximum THz signal level, the spatial resolution was estimated to be 36 μm, which is approximately $\lambda_0/10$, where $\lambda_0$ is the peak THz wavelength (0.9 THz). Roughly speaking, the spatial resolution of near-field THz wave imaging with a dynamic aperture created on a GaAs wafer is determined by the focal size of optical gating beam 24.

EXAMPLE 5

Figure 9A:
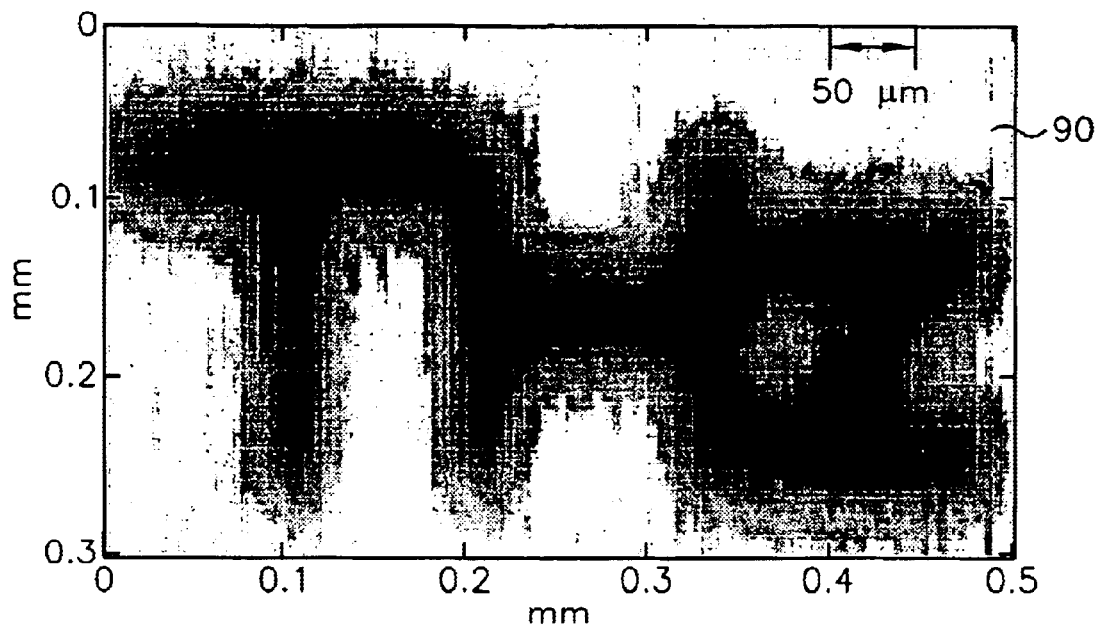
FIG. 9A shows an image derived by a dynamic aperture THz imaging method of the present invention of the word "THz" made by optically damaging a GaAs wafer.
Figure 9B:
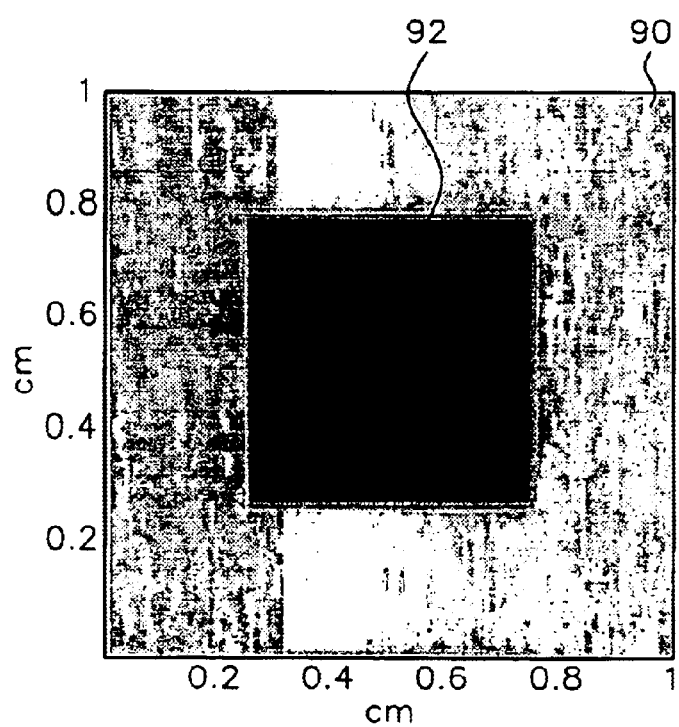
FIG. 9B shows an image derived by a dynamic aperture THz imaging method of the present invention of a square region made by optically damaging a GaAs wafer.
Figure 9C:
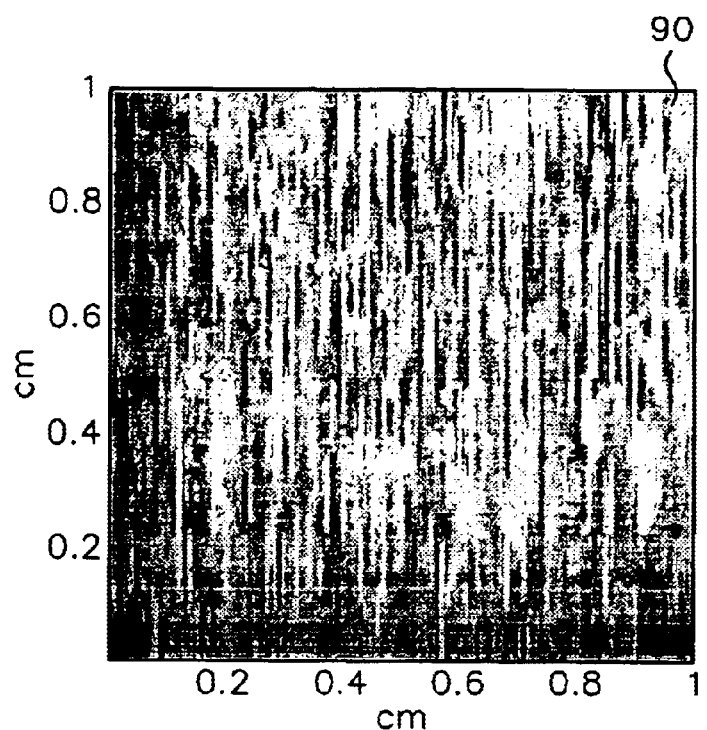
FIG. 9C shows an image derived by a THz imaging method of the prior art of the square shown in FIG. 9B.

To explore some unique imaging capabilities of the imaging system with a dynamic aperture, the letters "THz" were carved on the surface of a GaAs wafer 90 using a focused laser beam. The total size of the letters was within an area of 0.3 mm×0.5 mm. FIG. 9A shows the THz wave image of the letters "THz" obtained by using the dynamic aperture technique. Conventional THz wave imaging techniques cannot detect this kind of damage, as is illustrated by FIGS. 9B and 9C. FIG. 9B shows a square 92 having a larger area (5 mm×5 mm) that was damaged on wafer 90 and imaged using a dynamic aperture in accordance with this invention. FIG. 9C shows the same portion of wafer 90 imaged using a conventional THz wave imaging technique. The poor result occurs because conventional THz wave imaging is not sensitive to such a tiny change in the surface quality. The depth of THz wave modulation from the photocarriers in those two areas is different, however, owing to the difference of light absorption and photocarrier lifetime, and thus it is picked up by the dynamic aperture method of this invention. These results indicate that the dynamic aperture method has the potential to be used to characterize aspects of semiconductor surfaces such as the doping level and type, with a spatial resolution limited by the near-infrared wavelength and the near-field effect.

EXAMPLE 6

Figure 10A:
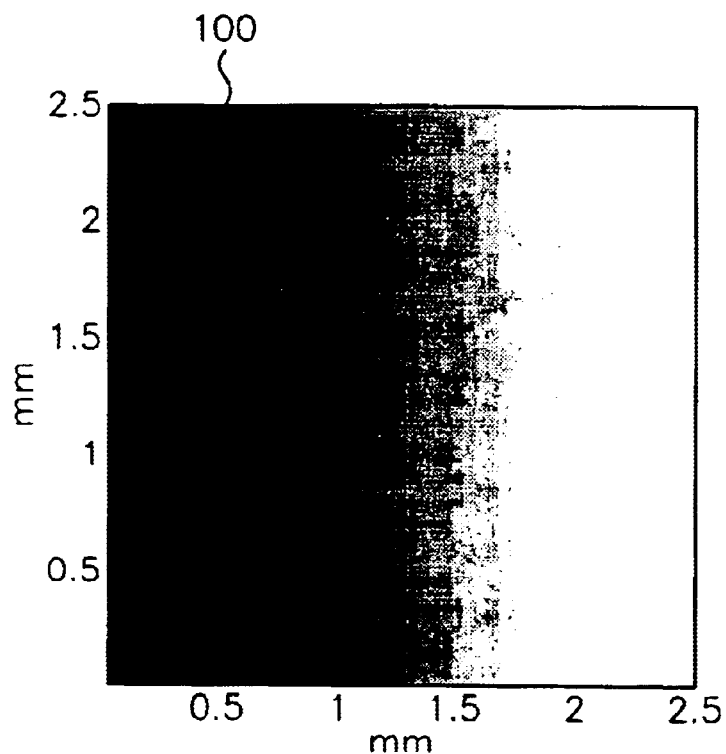
FIG. 10A shows an image derived by a dynamic aperture THz imaging method of the present invention of a p$^+$-doped annealed area on an n-doped silicon wafer.
Figure 10B:
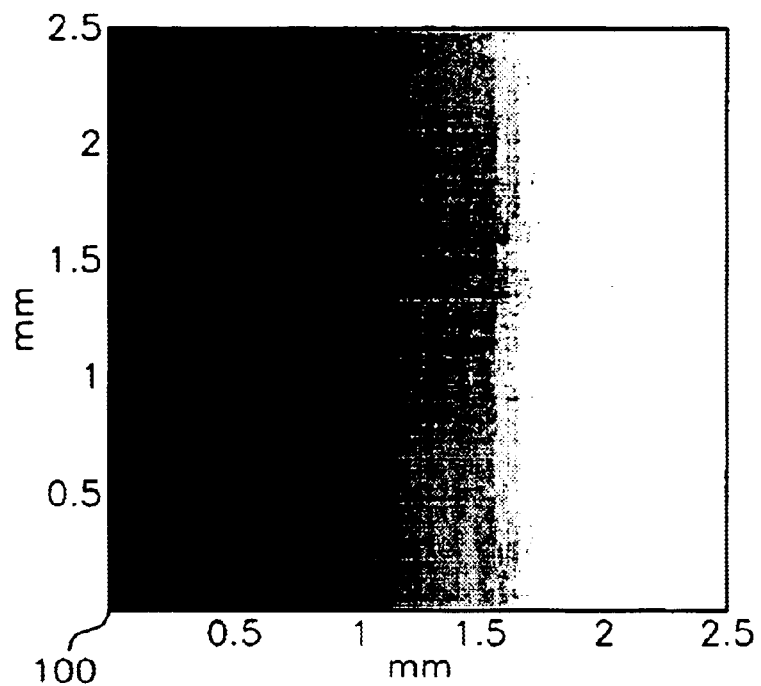
FIG. 10B shows the same area as in FIG. 10A derived by a THz imaging method of the prior art.

FIGS. 10A and 10B show THz wave images of a $p^+$-doped annealed area 100 on an n-doped silicon wafer, derived by using different techniques. Because the wafer conductivity is high in the doped and annealed area, conventional methods can distinguish, of course, the doped and undoped regions on the same silicon wafer, as shown in FIG. 10A. But the image obtained by the dynamic aperture method, shown in FIG. 10B, shows a spatial resolution that is much improved, which helps to locate the interface between the doped and undoped regions in a more accurate way.

Figure 10C:
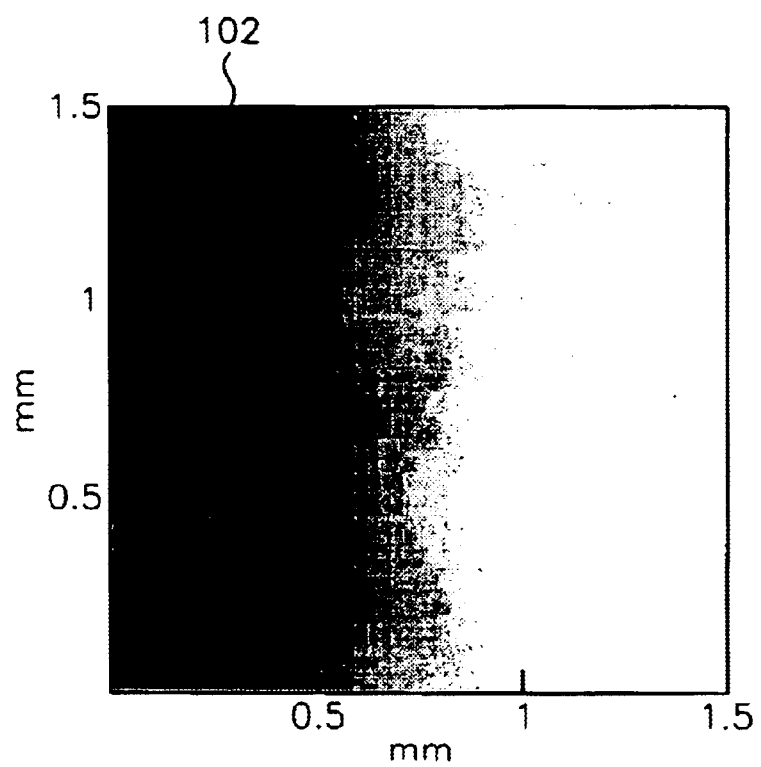
FIG. 10C shows an image derived by a dynamic aperture THz imaging method of the present invention of a p$^+$-doped unannealed area on an n-doped silicon wafer.
Figure 10D:
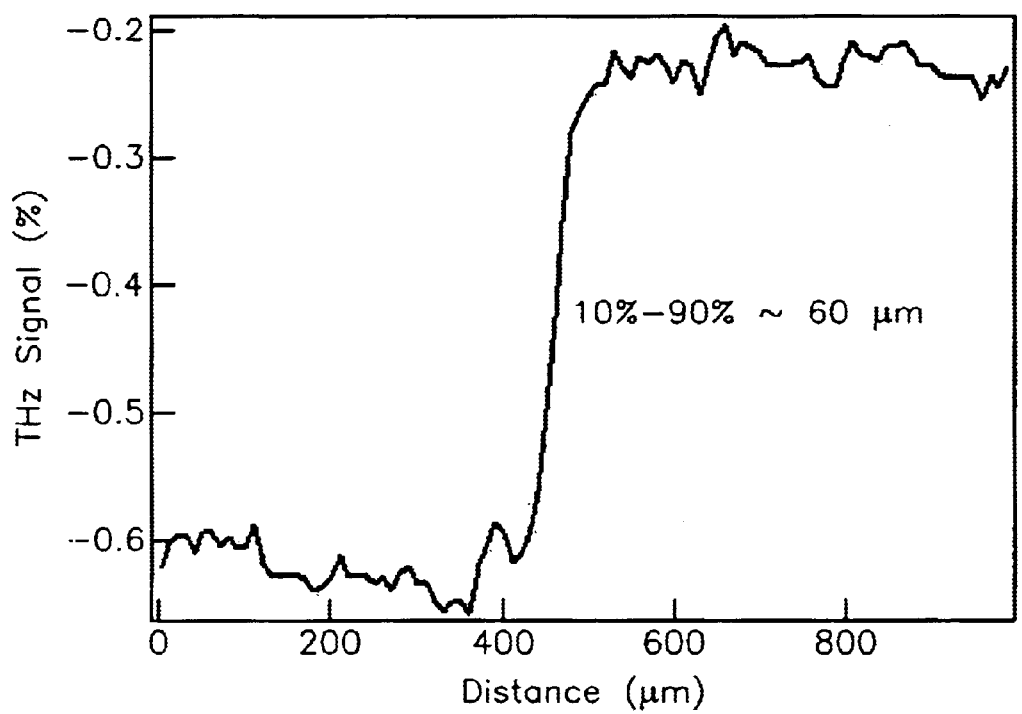
FIG. 10D shows a graph of distance in micrometers versus percentage of THz signal for the image derived by a dynamic aperture THz imaging method as shown in FIG. 10C.

FIG. 10C shows a THz wave image of a p+-doped unannealed area 102 on an n-doped silicon wafer obtained using a dynamic aperture. The gating beam power was 1.8 mW and its size was 22 μm. A scan across the p+-doped unannealed and n-doped areas indicates a spatial resolution of 60 μm instead of 22 μm, as shown in FIG. 10D. The reason for the relatively poor resolution as compared with the resolution achieved on the GaAs wafer, as described in Example 4, is that the THz signal detected with the above gating beam power was mainly from the modulation due to the temperature effect from previous pluses. The lifetime of the temperature effect is several milliseconds and the heat flow can diffuse locally due to the higher thermal conductivity of silicon.

The ability to image p+-doped unannealed areas on an n-doped silicon wafer is unique to the dynamic aperture technique described above. Such an image cannot be realized by conventional THz imaging methods because the resistivity of the p+-doped unannealed area on an n-doped silicon wafer is almost the same as that of the undoped area. The image shown in FIG. 10C could not be reproduced with a laser repetition rate decreased to 10 kHz and a gating power of 1.6 mW. Thus, the imaging mechanism of a p+-doped unannealed area on an n-doped silicon wafer is due to the THz wave modulation of the temperature effect instead of photocarriers. It further indicates that the p+-doped unannealed area, in comparison with the undoped area, has either a different variation of complex refractive index with the same local temperature increase, or a different temperature increase with the same gating beam power. Either way, the dynamic aperture technique of the present invention may be beneficial for characterization of semiconductor surface quality.

Although illustrated and described above with reference to certain specific embodiments, the present invention is nevertheless not intended to be limited to the details shown. Rather, various modifications may be made in the details within the scope and range of equivalents of the claims and without departing from the spirit of the invention. For example, although specific laser source types, pulse characteristics, and semiconductor types are detailed above in the specific examples, the invention is not limited to any of these specific details. Rather the invention is broadly applicable to the use of a dynamic aperture for THz imaging in any form.

What is claimed:

1. A system for using terahertz (THz) radiation to produce an image of an object, the system comprising:
    means for providing an optical pump pulse, an optical probe pulse having a polarization ellipticity, and an optical gating pulse with a variable delay time between the optical pump pulse and the optical probe pulse;
    a THz emitter for emitting a beam of THz radiation when activated by the optical pump pulse;
    means for chopping the optical gating pulse on and off;
    a layer of semiconductive material comprising (a) a part of the object, or (b) a discrete layer positioned between the object and the THz radiation;
    means for focusing the optical gating pulse and the THz radiation on the layer of semiconductive material so that the gating pulse illuminates a gating pulse focal spot on the layer of semiconductive material, the gating pulse focal spot having a diameter effective to cause measurable modulation in transmission of the THz radiation through the layer of semiconductive material when the gating pulse is on as compared to when the gating pulse is off, creating alternating modulated THz beams;
    a THz receiver, positioned to receive the alternating modulated THz beams reflected from or transmitted through the object, for modulating the optical probe pulse with the alternating modulated THz beams to create corresponding modulation in the optical probe pulse polarization ellipticity;
    means for converting the modulation in the optical probe pulse polarization ellipticity to intensity modulation in the optical probe pulse;
    means for converting the intensity modulated optical output pulse to electronic information; and
    means for receiving the electronic information and producing an image of the object from the electronic information.

2. The system of claim 1, wherein the THz emitter and the THz receiver each comprise an electro-optic crystal.

3. The system of claim 2, wherein each electro-optic crystal comprises ZnTe.

4. The system of claim 1, wherein the THz receiver and the THz emitter each comprise a photoconductive antenna.

5. The system of claim 1, wherein the THz beam has a THz beam focal spot that has a diameter greater than the diameter of the gating pulse focal spot.

6. The system of claim 5, wherein the means for focusing comprises means for aligning the gating pulse focal spot inside the THz beam focal spot.

7. The system of claim 1, further comprising means for providing a variable delay between the gating pulse and the THz beam.

8. The system of claim 7, wherein the means for providing a variable delay provides a delay of −5 to 20 picoseconds, wherein a negative delay means that the gating pulse arrives at the object after the THz beam.

9. The system of claim 1, further comprising means for varying the diameter of the gating pulse focal spot.

10. The system of claim 1, wherein the gating pulse focal spot has a diameter in a range of about 22 $\mu$m to 232 $\mu$m.

11. The system of claim 1, wherein the layer of semiconductive material has a thickness greater than an optical beam absorption thickness for the semiconductive material.

12. The system of claim 1, wherein the semiconductive material of the object comprises silicon or gallium arsenide.

13. The system of claim 1, wherein the object further comprises at least one region that is not semiconductive.

14. The system of claim 1, wherein the object further comprises at least one region that is doped.

15. The system of claim 14, wherein the doped region is annealed.

16. The system of claim 14, wherein the doped region is unannealed.

17. The system of claim 1, wherein the layer of semiconductive material is positioned between the object and the THz beam and on a surface of the object.

18. The system of claim 1, wherein the THz emitter and the THz receiver comprise a single THz transciever.

19. The system of claim 18, wherein the THz transceiver is positioned to receive a portion of the THz beam reflected from the object.

20. The system of claim 1, wherein the THz emitter and the THz receiver are separate elements and the THz receiver is positioned to receive a portion of the THz beam transmitted through the object.

21. A system for using terahertz (THz) radiation to produce an image of an object, the system comprising:
    a laser source providing an optical pump pulse, an optical probe pulse having a polarization ellipticity, and an optical gating pulse;
    a delay stage providing a variable delay time between the optical pump pulse and the optical probe pulse;
    a delay stage providing a variable delay time between the optical gating pulse and the optical pump pulse;

a chopper turning the optical gating pulse on and off;

a THz emitter for emitting a beam of THz radiation when activated by the optical pump pulse;

a layer of semiconductive material comprising (a) a part of the object, or (b) a discrete layer positioned between the object and the THz radiation;

optics focusing the THz beam on the layer of semiconductive material;

a lens focusing the optical gating pulse on the layer of semiconductive material so that the gate pulse illuminates a gate pulse focal spot on the layer of semiconductive material, the gating pulse focal spot having a diameter effective to cause measurable modulation in transmission of the THz beam through the layer of semiconductive material when the gating pulse is on as compared to when the gating pulse is off, creating alternating modulated THz beams which illuminate the object;

a THz receiver, positioned to receive the alternating modulated THz beams reflected from or transmitted through the object, modulating the optical probe pulse with the alternating modulated THz beams to create corresponding modulation in the optical probe pulse polarization ellipticity;

a polarizer converting the modulation in the optical probe pulse polarization ellipticity to intensity modulation in the optical probe pulse;

a photodetector converting the intensity modulated optical output pulses to electronic information; and a processor receiving the electronic information and producing an image of the object from the electronic information.

22. The system of claim 21, wherein the THz emitter and the THz receiver comprise a single THz transciever positioned to receive a portion of the THz beam transmitted through the object.

23. The system of claim 21, wherein the THz emitter and the THz receiver comprise separate elements and the THz receiver is positioned to receive a portion of the THz beam reflected from the object.

24. A method for using THz radiation to generate an image of an object, the method comprising the steps of:

(a) providing an optical pump pulse, an optical probe pulse having a polarization ellipticity, and an optical gating pulse with a variable delay time between the optical pump pulse and the optical probe pulse;

(b) activating a THz emitter with the optical pump pulse to emit a beam of THz radiation;

(c) chopping the optical gating pulse on and off;

(d) providing a layer of semiconductive material that is either (i) part of the object, or (ii) a discrete layer placed between the object and the THz beam;

(e) focusing the optical gating pulse and the THz beam on the layer of semiconductive material so that the gating pulse illuminates a gating pulse focal spot on the layer of semiconductive material, the gating pulse focal spot having a diameter effective to cause measurable modulation in transmission of the THz beam through the layer of semiconductive material when the gating pulse is on as compared to when the gating pulse is off, creating alternating modulated THz beams while illuminate the object;

(f) modulating the optical probe pulse with the alternating modulated THz beams in a THz receiver, positioned to receive the alternating modulated THz beams reflected from or transmitted through the object, to create corresponding modulation in the optical probe pulse polarization ellipticity;

(g) converting the modulation in the optical probe pulse polarization ellipticity to intensity modulation in the optical probe pulse;

(h) detecting the intensity modulation in the optical probe pulse and converting the intensity modulation to electronic information; and (i) receiving and processing the electronic information to produce the image of the object.

25. The method of claim 24, comprising using an electro-optic crystal for the THz emitter and an electro-optic crystal for the THz receiver.

26. The method of claim 24, comprising using a photoconductive antenna for the THz receiver and a photoconductive antenna for the THz emitter.

27. The method of claim 24, comprising providing the THz beam with a THz beam focal spot that has a diameter greater than the diameter of the gating pulse focal spot.

28. The method of claim 27, comprising aligning the gating pulse focal spot inside the THz beam focal spot.

29. The method of claim 24, further comprising providing a variable delay between the gating pulse and the THz beam.

30. The method of claim 29, comprising providing a variable delay in a range of −5 to 20 picoseconds, wherein a negative delay means that the gating pulse arrives at the object after the THz beam.

31. The method of claim 24, further comprising varying the diameter of the gating pulse focal spot.

32. The method of claim 31, comprising varying the gating pulse focal spot diameter within a range of about 22 $\mu$m to 232 $\mu$m.

33. The method of claim 24, comprising generating the image for an object comprising silicon.

34. The method of claim 24, comprising generating the image for an object comprising gallium arsenide.

35. The method of claim 24, comprising generating the image for an object comprising at least one region that is not semiconductive.

36. The method of claim 24, comprising generating the image for an object comprising at least one region that is doped.

37. The method of claim 36, wherein the doped region is an annealed region.

38. The method of claim 36, wherein the doped region is an unannealed region.

39. The method of claim 24, comprising using a single THz transciever for the THz emitter and the THz receiver.

40. The method of claim 24, wherein the measurable modulation in transmission of the THz beam through the layer of semiconductive material is caused by generation of photocarriers within the semiconductive material.

41. The method of claim 40, wherein the semiconductive material comprises gallium arsenide.

42. The method of claim 24, wherein the measurable modulation in transmission of the THz beam through the semiconductor is caused by a temperature effect within the semiconductive material.

43. The method of claim 42, wherein the semiconductive material comprises silicon.

44. The system of claim 24, wherein the laser source comprises a Ti:sapphire laser and each of the THz transmitter and the THz receiver comprise a ZnTe electro optic crystal.

45. A method of improving spatial resolution of a pump-probe THz imaging system for producing an image of an object comprising a semiconductive material, the improvement comprising the step of providing a chopped optical gating beam focused on the object in a gating pulse focal spot, the gating pulse focal spot having a diameter effective to cause measurable Modulation in transmission of a THz beam through the object when the gating pulse is on as compared to when the gating pulse is off, creating alternating modulated THz beams for detection and processing.

46. A method of improving spatial resolution of a pump-probe THz imaging system for producing an image of an object using a THz beam, the improvement comprising the step of placing a layer of semiconductive material between the object and the THz beam and providing a chopped optical gating beam focused on the layer of semiconductive material in a gating pulse focal Spot, the gating pulse focal spot having a diameter effective to cause measurable modulation in transmission of the THz beam through the layer of semiconductive material when the gating pulse is on as compared to when the gating pulse is off, creating alternating modulated THz beams for detection and processing.

* * * * *